US007985734B2

(12) United States Patent
Cheng et al.

(10) Patent No.: US 7,985,734 B2
(45) Date of Patent: Jul. 26, 2011

(54) PEPTIDES FOR PREVENTING OR TREATING LIVER DAMAGE

(75) Inventors: Yun Cheng, Beijing (CN); Ruihe Yu, Beijing (CN); Wan Zhou Zhao, Beijing (CN); Jun Zhao, Beijing (CN); Jing Li, Beijing (CN)

(73) Assignees: Yun Cheng, Beijing (CN); Ruihe Yu, Beijing (CN)

( * ) Notice: Subject to any disclaimer, the term of this patent is extended or adjusted under 35 U.S.C. 154(b) by 509 days.

(21) Appl. No.: 12/066,636

(22) PCT Filed: Jun. 1, 2006

(86) PCT No.: PCT/CN2006/001176
§ 371 (c)(1),
(2), (4) Date: Mar. 12, 2008

(87) PCT Pub. No.: WO2007/137456
PCT Pub. Date: Dec. 6, 2007

(65) Prior Publication Data
US 2008/0227723 A1    Sep. 18, 2008

(51) Int. Cl.
*A61K 38/08* (2006.01)
(52) U.S. Cl. ............ 514/16; 514/17; 530/328; 530/329
(58) Field of Classification Search ........................ None
See application file for complete search history.

(56) References Cited

U.S. PATENT DOCUMENTS 5,709,995 A    1/1998 Chisari et al.

FOREIGN PATENT DOCUMENTS

| CN | 1194986 C | 3/2005 |
| CN | 1216075 C | 8/2005 |
| WO | WO 03/097677 A2 | 11/2003 |

OTHER PUBLICATIONS

Encke et al. :"Development of a heterologous, multigenotype vaccine against hepatitis C virus infection" Europ. J. of Clin. Inves. vol. 37, pp. 396-406. 2007.*
Ou-Yang et al. "Co-Delivery of GM-CSF Gene Enhances the Immune Responses of Hepatitis C Viral Core Protein-Expressing DNA Vaccine: Role of Dendritic Cells." J. of Med. Virol. bol. 66, pp. 320-328. 2002.*
Abrignani et al. Perspectives for a vaccine against hepatitis C virus. J. of Hepatology. VOl. 31, Supp. 1, pp. 259-263. 1999.*
Houghton et al. Prospects for a Vaccine against the Hepatitis C virus. Nature, vol. 436, pp. 961-966. Aug. 2005.*
Chi et al. "Cytokines secretion by peripheral blood mononuclear cells (PBMC) from hepatitis C patients after stimulation with synthetic peptides at the highly variable region (HVR1)." Chinese J. Exp. Clin. Virol. vol. 19, No. 3, pp. 279-281. Sep. 2005 (English Abstract included).*
Bain et al. Effects of HCV Viral Dynamics on Treatment Design: Lessons Learned from HIV. American Journal of Gastroenterology. vol. 96, No. 10, pp. 2818-2828. 2001.*
Hepatitis C. Mayoclinic.com. [online]. Retrieved on May 1, 2010. Retrieved from the Internet: <URL: http://www.myoclinic.com/health/hepatitis-C/DS00097/METHOD=print>. pp. 1-9.*
Zhao et al. "DNA immunization of mice with plasmid encoding mimic epitopes of hypervariable region 1 of hepatitis C virus" Acta Academiae Mediciniae Militaris Tertiae. vol. 26, No. 24, pp. 2254-2257. Dec. 2004.*
Choo et al. "Genetic organization and diversity of the hepatitis C virus" Proc. Natl. Acad. Sci. USA (88) Mar. 1991, p. 2451-2455.
Choo et al. "Isolation of a cDNA Clone Derived from a Blood-Borne Non-A, Non-B Viral Hepatitis Genome" Science (244) Apr. 21, 1989, p. 359-362.
Han et al. "Characterization of the terminal regions of hepatitis C viral RNA: identification of conserved sequences in the 5' untranslated region and poly(A) tails at the 3' end" Proc. Natl. Acad. Sci. USA (88) Mar. 1991, p. 1711-1715.
Shirai et al. "T Cell Recognition of Hypervariable Region-1 from Hepatitis C Virus Envelope Protein with Multiple Class II MHC Molecules in Mice and Humans: Preferential Help for Induction of Antibodies to the Hypervariable Region" The Journal of Immunology (162) 1999, p. 568-576.
Manns et al. Peginterferon alfa-2b plus ribavirin compared with interferon alfa-2-b plus ribaviririn for initial treatment of chronic hepatitis C: a randomised trial. The Lancet (358) Sep. 22, 2001, p. 958-965.
Nelson et al. The Role of Hepatitis C Virus-Specific Cytotoxic T Lymphocytes in Chronic Hepatitis C. The Journal of Immunology (158) 1997, p. 1473-1481.
Wong et al. Liver-Derived CTL in Hepatitis C Virus Infection: Breadth and Specificity of Responses in a Cohort of Persons with Chronic Infection. The Journal of Immunology (160) 1998, p. 1479-1488.
Ruggieri et al. "Sensitization to Fas-Mediated Apoptosis by Hepatitis C Virus Core Protein" Virology (229) 1997, p. 68-76.
International Search Report and Written Opinion of the International Searching Authority for International Application No. PCT/CN2006/001176, 2007.

* cited by examiner

*Primary Examiner* — Anish Gupta
(74) *Attorney, Agent, or Firm* — Hamre, Schumann, Mueller & Larson, P.C.

(57) ABSTRACT

The application of a peptide having sequence of formula I or its derivant in preparing the medicine for preventing or treating liver damage, especially liver damage and hepatitis C is disclosed, Xaa1-Gln-Xaa2-Xaa3-Thr-Ser-Gly-Xaa4 (formula I) wherein, Xaa1 is deletion, Ala, Gly, Val, Leu or Ile, Xaa2 is Thr or Ser, Xaa3 is Tyr, Phe or Trp, and Xaa4 is deletion, Ala, Gly, Val, Leu, Ile or Pro. The composite medicine containing the said peptide, its preparation method, and the polynucleotide for coding the said peptide are also disclosed.

4 Claims, 4 Drawing Sheets

PEPTIDES FOR PREVENTING OR TREATING LIVER DAMAGE

FIELD OF THE INVENTION

The present invention relates to the use of an immunogenic peptide of Hepatitis C virus or a derivative thereof in preventing or treating liver damage, preferably relates to the use of the peptide or a derivative thereof in preventing or treating immunological liver damage or hepatotoxic chemical substance-induced liver damage, and to the use in preventing or treating Hepatitis C. The present invention also relates to a pharmaceutical composition comprising the peptide or a derivative thereof, a method of manufacturing the peptide and a polynucleotide encoding the peptide.

BACKGROUND OF THE INVENTION

Viral hepatitis is a group of severe diseases that do harm to human health, the causative agents of which are a group of different hepatovirus. There are 7 types of hepatitis virus found hitherto, which are HAV, HBV, HCV, HDV, HEV and possible TTV and HGV. Among them, Hepatitis C virus (HCV) is a causative agent that results in Hepatitis C. Though Hepatitis C was originally identified as non-A, non-B hepatitis acquired by transfusion, the subsequent research showed that Hepatitis C virus is propagated not only by transfusion, but also by other ways via alimentary tract, sex act and so on. At present there are approximately more than 100 million persons infected with HCV in the world, and approximately 50%-90% of those persons will develop chronic disease. 8-46% and 11-19% from those with chronic disease will further develop hepatocirrhosis and hepatocellular carcinoma respectively.

HCV is a kind of RNA virus of Flavividae family. The studies (see, e.g., Choo et al, Science 244:359-362 (1989); Choo et al, Proc. Natl. Acad. Sci. USA 88:2451-2455 (1991); Han et al, Proc. Natl. Acad. Sci. USA 88: 1711-1715 (1991)) indicated that the HCV genome is a single positive RNA strand of about 9.4 kb and has an open reading frame (ORF) that nearly spans the whole genome. The ORF encodes a viral ployprotein precursor of 3011 or 3010 amino acids. The proteins encoded by the HCV genome include the nucleocapsid core protein(C), the two envelope glycoproteins (E1 and E2), and the genome contains five regions corresponding to non-structural proteins (NS1~NS5). In the genome, the hypervariable region 1 (HVR1) from E2 region of Hepatitis C virus contains important antigenic epitopes that can induce neutralizing antibodies (see, e.g., Shirai et al, J. Immunol, 162:568-576(1999)). However, the gene of HVR1 may be greatly mutated due to immunological selection so that HCV can escape from the recognition of the body immune system. This might be the major cause whereby HCV results in chronic hepatitis.

At present, the mechanism whereby HCV causes disease is not well understood, and there are no very clinically effective therapeutic methods and vaccines to prevent its propagation. Interferon (IFN) is often used in the current clinical therapy to degrade viral RNA by activating RNase L, but the long-term effective rate of the therapy is only about 20%. Manns et al (The Lancet, 358: 958-965 (2001)) treated Hepatitis C by using both of pegylated interferon and ribavirin. While this therapy is particularly effective in the case of patients infected by viral strains belonging to genotypes 2 and 3, it only has a limited effect on genotypes 1a, 1b and 4. Therefore, people have tried by a variety of means to research and develop vaccines that decrease HCV infection and medicines that cure hepatitis.

From the study of the HCV genome, people have found a number of immunogenic peptides against HCV, which can induce an immune response to HCV in the body. For example, U.S. Pat. No. 5,709,995A of Chisari et al discloses a group of peptides that stimulate HCV-specific cytotoxic T lymphocyte (CTL). WO2003/097677A discloses HCV antigenic peptides and compositions thereof, which have the ability to induce strong immune responses. CN1194986C and CN1216075C of the inventor of the present invention also disclose a group of HCV immunogenic peptides that can induce the generation of antibodies. Although it was thought in the early time that HCV caused liver damage by virus-induced cytopathy like certain viruses (e.g., Hepatitis C virus, EB virus), the recent studies indicated that the immune response against HCV is the major cause leading to liver damage. Particularly in chronic patients with HCV, the lymphocyte (especially cytotoxic T lymphocyte) can not completely effectively eliminate HCV, but in the process of eliminating hepatocytes infected with HCV, it results in immunological hepatocyte damage, and thus leads to hepatocyte apoptosis and even to hepatocirrhosis and hepatocellular carcinoma (see, for example, Nelson et al, J. Immunol., 158:1473-1481(1997); Wong et al, J. Immunol., 160:1479-1488 (1998); Ruggieri et al, Virology, 229: 68-76 (1997)). Therefore, the HCV immunogenic peptide used as vaccine will induce an immune response against HCV that might lead to immunological liver damage. Practically, such mechanism greatly impedes the development of prophylactic vaccine or therapeutical medicine for Hepatitis C (especially chronic Hepatitis C) from such HCV immunogenic peptides.

Except immunological liver damage and pathogenic liver damage, it is well known that hepatotoxic chemical substance can also induce liver damage. It is known that some drugs can cause liver damage, and result in hepatic cytolysis and necrosis. For example, the analgetic acetaminophen (i.e., Panadol, the chemical name of which is 4-(N-acetylamino)phenol), when administrated in a large dose, is a kind of liver-damaging substance that can induce necrosis of human liver. For example, long-term administration of antibiotic, such as rifampicin, pyrazinamide, and isoniazide, and long-term administration of estrogen and the like in the period of menopause, also can cause severe hepatocyte necrosis, leading to liver damage, such as acute or chronic hepatitis, jaundice, and hepatic fibrosis and the like. The liver-damaging substances include substance that can generate many active free radicals, particularly include substance that can generate oxygen-derived free radicals, which induce hepatotoxity via oxidation.

After massive research, the inventor obtained an HCV immunogenic peptide and derivative thereof that can prevent or treat liver damage, and surprisingly, the said liver damage is not limited to immunological damage of hepatocyte infected with HCV. For example, the peptide and derivative thereof of the invention can be used to prevent or treat immunological liver damage, pathogenic liver damage and hepatotoxic chemical substance-induced liver damage.

DESCRIPTION OF THE INVENTION

The invention relates to a peptide and derivative thereof, which can be used for preventing or treating liver damage in addition to inducement of immune response against HCV, particularly for preventing or treating immunological liver damage, wherein the said liver damage is not limited to immunological damage of hepatocyte infected with HCV.

In the first aspect, the invention provides a use of a peptide having the sequence of Formula I (SEQ ID NO.: 1) or a pharmaceutically acceptable salt or ester thereof, Xaa1-Gln-Xaa2-Xaa3-Thr-Ser-Gly-Xaa4 (Formula I)

wherein,
Xaa1 is absent, Ala, Gly, Val, Leu or Ile,
Xaa2 is Thr or Ser,
Xaa3 is Tyr, Phe or Trp, and
Xaa4 is absent, Ala, Gly, Val, Leu, Ile or Pro,
and the said use is for preventing or treating liver damage or for the manufacture of a medicament for preventing or treating liver damage. Namely, the invention provides a use of a peptide having the sequence of Formula I or a pharmaceutically acceptable salt or ester thereof in preventing or treating liver damage, and provides a use of a peptide having the sequence of Formula I or a pharmaceutically acceptable salt or ester thereof in the manufacture of a medicament for preventing or treating liver damage.

The phrase "liver damage", when used herein, refers to injury or pathological change present in liver tissue or cell. The clinical conditions of liver damage include degeneration of live cells, vasculitis of liver, spotty necrosis or focal necrosis present in liver, inflammatory cell infiltration or fibroblast proliferation in liver and portal area, or hepatomegaly, and hepatocirrhosis, hepatoma resulted from severe liver damage, and the like. For evaluation of liver damage, in addition to pathological conditions as mentioned above, determination of aminotransferase activity in serum can be used to diagnose the damage of liver and to assess the degree of damage, because due to cytolysis of damaged liver cells, the amount of the circulating aminotransferase released from damaged liver cells increases. In the embodiment of the invention, the liver damage can be determined by measuring the level of glutamic-pyruvic transaminase or glutamic-oxalacetic transaminase. Preferably in the invention, the liver damage can be liver damage indicated by the level of glutamic-pyruvic transaminase or glutamic-oxalacetic transaminase in serum, and the indication of curative effect on prevention or treatment of liver damage can be the decrease in the level of glutamic-pyruvic transaminase or glutamic-oxalacetic transaminase. The effect of the peptide having the sequence of Formula I of the invention or a pharmaceutically acceptable salt or ester thereof on liver damage can be determined from the alleviation of pathological conditions as mentioned above and the decrease in the level of glutamic-pyruvic transaminase or glutamic-oxalacetic transaminase.

Current study has found that a variety of hepatotoxic drugs and chemical substance, immunogen or pathogen can cause liver damage. Preferably the liver damage as mentioned in the invention is immunological liver damage or hepatotoxic chemical substance-induced liver damage. Namely, the invention preferably provides a use of a peptide having the sequence of Formula I or a pharmaceutically acceptable salt or ester thereof in preventing or treating immunological liver damage or hepatotoxic chemical substance-induced liver damage, and preferably provides a use of a peptide having the sequence of Formula I or a pharmaceutically acceptable salt or ester thereof in the manufacture of a medicament for preventing or treating immunological liver damage or hepatotoxic chemical substance-induced liver damage. At present, there are a variety of animal models used to assess the effect on liver damage in the invention. In a specific example, the peptide of the invention can alleviate immunological liver damage induced by BCG vaccine and lipopolysaccharide. In addition, in a specific model of hepatotoxic chemical substance-induced liver damage, the peptide of the invention can prevent liver damage induced by D-aminogalactose, and the peptide of the invention can also treat liver damage induced by tetrachloromethane.

A "peptide having the sequence of Formula I" used in the invention, refers to a peptide of the sequence of Formula I or a modified functional equivalent thereof. Namely, the peptide of the sequence of Formula I may not be modified at its amino group at N-terminus, carboxyl group at C-terminus and groups at side chains of amino acids therein, or may be modified without substantially diminishing its effect on prevention or treatment of liver damage. A "functional equivalent" used herein refers to a modified product comprising the sequence of Formula I, of which the effect on prevention or treatment of liver damage is not substantially diminished, namely the effect of prevention or treatment of liver damage is diminished by less than 50%, preferably by less than 30%, more preferably by less than 10%, and most preferably not diminished. Some pathological conditions or levels of some aminotransferases in serum can be used to determine the effect of a functional equivalent on prevention or treatment of liver damage, preferably the pathology score criterion or the level of glutamic-pyruvic transaminase or glutamic-oxalacetic transaminase in serum as mentioned in the embodiment of the invention is used to determine the effect.

For the peptide of the invention, suitable modifications include, for example, cyclization, polymerization, modification at the terminal amino group, carboxyl group or side chain groups to form a pharmaceutically acceptable ester, conjugation to form a conjugate comprising the sequence of Formula I, fusion to form a fusion protein comprising the sequence of Formula I, or combinations thereof, etc. In general, a linear peptide can be cyclized, for example, by linking the N-terminal amino group of the peptide to the C-terminal carboxyl group of the peptide to form a cyclic peptide, to prolong its half-life in the physiological environment. A "pharmaceutically acceptable ester" refers to an ester suitable for contact with human or animal tissues without leading to various toxicity, stimulation or allergy, etc. Generally, esterification of a peptide can reduce proteolysis by proteases in the body. The peptide of the invention can be modified at the terminal amino group, carboxyl group or side chain groups to form a pharmaceutically acceptable ester. Modifications at side chain groups include, but are not limited to, esterification between the side chain group of threonine or serine and carboxylic acid. Modifications at N-terminal amino group include, but are not limited to, deamination, and modification with N-lower alkyl, N-di-lower alkyl and N-acyl. Modifications at C-terminal carboxyl group include, but are not limited to, modification to be amide, lower alkyl amide, dialkyl amide, and lower alkyl ester. Preferably, the terminal groups are protected by protective groups known to a skilled person in the field of protein chemistry, such as acetyl, trifluoroacetyl, Fmoc (9-fluorenyl-methoxycarbonyl), Boc (teriary butoxycarbonyl), Alloc (allyloxycarbonyl), $C_{1-6}$ alkyl, $C_{2-8}$ alkenyl, $C_{7-9}$ aralkyl, etc. In an embodiment of the invention, preferably the peptide of Formula I is not modified at N-terminal amino group, C-terminal carboxyl group and side chain groups of amino acids therein, namely the group at N-terminus remains α-amino group (—$NH_2$) of the first amino acid, the group at C-terminus remains carboxyl group (—COOH) of the C-terminal amino acid. Preferably in the invention, C-terminal carboxyl group can also be amidated, namely the group at C-terminus is —CO $NH_2$.

Using methods known in the art, a conjugate comprising the sequence of Formula I may comprise a pharmaceutically acceptable water-soluble polymer moiety. In general, such conjugate can be shown to enhance the circulating half-life of the peptide of the sequence of Formula I. Suitable water-soluble polymers include polyethylene glycol (PEG), monomethoxy-PEG, mono-($C_{1-C10}$)alkoxy-PEG, aryloxy-PEG, poly-(N-vinyl pyrrolidone)PEG, trimethoxy PEG, monomethoxy-PEG propionaldehyde, PEG propionaldehyde, disuccinimidyl carbonate PEG, propylene glycol homopolymers, a polypropylene oxide/ethylene oxide co-polymer, polyoxyethylated polyols (e.g., glycerol), monomethoxy-PEG butyraldehyde, PEG butyraldehyde, monomethoxy-PEG acetaldehyde, PEG acetaldehyde, methoxyl PEG-succinimidyl propionate, methoxyl PEG-succinimidyl butanoate, polyvinyl alcohol, dextran, cellulose, or other carbohydrate-based polymers. Suitable PEG may have a molecular weight from about 600 to about 60,000, including, for example, 5,000 daltons, 12,000 daltons, 20,000 daltons, 30,000 daltons, and 40,000 daltons, which can be linear or branched. A conjugate comprising the sequence of Formula I can also comprise a mixture of such water-soluble polymers. Pegylation can be carried out by any of the PEGylation reactions known in the art (see, for example, Delgado et al, Critical Reviews in Therapeutic Drug Carrier Systems 9:249 (1992), Duncan and Spreafico, Clin. Pharmacokinet. 27:290 (1994), and Francis et al, Int J Hematol 68: 1 (1998)). For example, Pegylation can be performed by an acylation reaction or by an alkylation reaction with a reactive polyethylene glycol molecule. In an alternative approach, a conjugate are formed by condensing activated PEG, in which a terminal hydroxy or amino group of PEG has been replaced by an activated linker (see, for example, Karasiewicz et al, U.S. Pat. No. 5,382,657A). A conjugate comprising the sequence of Formula I also may be a conjugate formed by the couple of the peptide of the sequence of Formula I to other proteins. The said other proteins include human albumin, bovine albumin, or Fc portion of IgG molecule. In an embodiment of the invention, the peptide of the invention is coupled to bovine albumin to form a peptide conjugate.

A peptide having the sequence of Formula I of the invention also may be a fusion peptide or fusion protein comprising the sequence of Formula I, which is formed by the peptide of the sequence of Formula I fused to other peptide or protein. The said other protein may be human albumin, bovine albumin, or Fc portion of IgG molecule. Albumin can be genetically coupled a peptide having the sequence of Formula I of the invention to prolong its half-life. And human albumin is the most prevalent naturally occurring blood protein in the human circulatory system, persisting in circulation in the body for over 20 days. Research has shown that therapeutic proteins genetically fused to human albumin have longer half-lives. And other research has shown that the resultant fusion protein fused with Fc portion may have an increased circulating half-life (See, U.S. Pat. No. 5,750,375A, U.S. Pat. No. 5,843,725A, U.S. Pat. No. 6,291,646; Barouch et al, Journal of Immunology, 61:1875-1882 (1998); Barouch et al, Proc. Natl. Acad. Sci. USA, 97(8):4192-4197 (Apr. 11, 2000); and Kim et al, Transplant Proc, 30(8):4031-4036 (December 1998)).

In the peptide having the sequence of Formula I of the invention, preferably Xaa1 is Gly, Xaa2 is Thr, Xaa3 is Tyr, and Xaa4 is absent (SEQ ID NO.: 2), Ala (SEQ ID NO.: 3) or Gly (SEQ ID NO.: 4), more preferably Xaa4 is absent. "Absent" used herein refers to the absence of the absent amino acid residue in the peptide sequence. For example, when Xaa4 is absent, the amino acid at C-terminus of the sequence of Formula I is Gly in Formula I.

All symbols of the peptide, amino acid, and group used herein are well known in the art. The abbreviations of amino acids or amino acid residues are defined in Table 1, and these abbreviations may represent L-amino acids, or may represent D-amino acids, preferably represent L-amino acids. The amino acids or amino acid residues can be divided according to the similarity of properties of amino acid side chains into the following groups: hydrophobic amino acids (A, I, L, M, F, P, W, Y, V), hydrophilic amino acids (R, D, N, C, E, Q, G, H, K, S, T), amino acids having an aliphatic side chain (G, A, V, L, I, P), amino acids having a hydroxyl group-containing side chain (S, T, Y), amino acids having a sulfur-containing side chain (C, M), amino acids having a carboxylic acid- or amide-containing side chain (D, N, E, Q), amino acids having a base-containing side chain (R, K, H), and amino acids having an aromatic-containing side chain (H, F, Y, W). The amino acids or amino acid residues within the same group generally have similar properties.

TABLE 1 the Abbreviations of Amino Acids

| Amino Acid | Three Letter Code | One Letter Code |
|---|---|---|
| alanine | Ala | A |
| arginine | Arg | R |
| asparagine | Asn | N |
| aspartic acid | Asp | D |
| cysteine | Cys | C |
| glutamine | Gln | Q |
| glutamic acid | Glu | E |
| glycine | Gly | G |
| histidine | His | H |
| isoleucine | Ile | I |
| leucine | Leu | L |
| lysine | Lys | K |
| methionine | Met | M |
| phenylalanine | Phe | F |
| proline | Pro | P |
| serine | Ser | S |
| threonine | Thr | T |
| tryptophan | Trp | W |
| tyrosine | Tyr | Y |
| valine | Val | V |

A "pharmaceutically acceptable salt" refers to a salt suitable for contact with human or animal tissues without leading to various toxicity, stimulation or allergy, etc. A pharmaceutically acceptable salt is well known in the art. Such salt may be prepared in the process of final isolation and purification of the peptide of the invention, or may be prepared by a further reaction with a suitable organic or inorganic acid or base. The representative acid addition salts include, but are not limited to, acetate, dicaproate, alginate, citrate, asprtate, benzoate, benzenesulphonate, bisulfate, butyrate, camphorate, camphorsulfonate, glycerophosphate, sulfite, heptylate, hexanoate, fumarate, hydrochlorate, hydrobromide, hydriodate, 2-hydroxyethylsulphonate, lactate, maleate, mesylate, nicotinate, 2-naphthalenesulfonate, oxalate, 3-phenylpropionate, propionate, succinate, tartrate, phosphate, glutamate, bicarbonate, p-toluene sulfonate, and undecanate. The preferable acids used to form pharmaceutically acceptable salts are hydrochloric acid, hydrobromic acid, sulfuric acid, phosphoric acid, oxalic acid, maleic acid, succinic acid, and citric acid. The cations in pharmaceutically acceptable base addition salts include, but are not limited to, ions of alkali metals or alkaline earth metals such as potassium, calcium, magnesium, and aluminium, and cations of nontoxic quaternary ammoniums such as ammonium, tetramethyl ammonium, tetraethyl ammonium, methylamine, dimethylamine, trimethylamine, triethylamine, diethylamine, ethylamine, ethanolamine, diethanolamine, piperidine, piperazine, and the like. The preferable salts include phosphate, tris, and acetate.

Such salts may generally increase the solubility of peptides without substantially altering their activity. The peptide of the invention may be utilized itself, or utilized in the form of pharmaceutically acceptable salt.

The use of the first aspect of the invention may further include the use for preventing and/or treating Hepatitis C. Namely, in addition to the prevention or treatment of liver damage, the invention further provides a use of a peptide having the sequence of Formula I or a pharmaceutically acceptable salt or ester thereof in preventing or treating liver damage and Hepatitis C simultaneously, and provides a use of a peptide having the sequence of Formula I or a pharmaceutically acceptable salt or ester thereof in the manufacture of a medicament for preventing or treating liver damage liver damage and Hepatitis C simultaneously. The peptide of the invention has the ability to induce cytokines such as γ-IFN, IL-4, and IL-10, and antibodies. Among them, γ-IFN, a significant cytokine secreted from Class I helper T cell (Th1), is one of important cytokines against virus infection in immune system of the body, which can induce cellular immune response against HCV to eliminate HCV, and has been used in the current well-established HCV therapy.

In the second aspect, the invention provides a pharmaceutical composition comprising a peptide having the sequence of Formula I or a pharmaceutically acceptable salt or ester thereof and a pharmaceutically acceptable carrier, Xaa1-Gln-Xaa2-Xaa3-Thr-Ser-Gly-Xaa4    (Formula I)

wherein,
Xaa1 is absent, Ala, Gly, Val, Leu or Ile,
Xaa2 is Thr or Ser,
Xaa3 is Tyr, Phe or Trp, and
Xaa4 is absent, Ala, Gly, Val, Leu, Ile or Pro,
for the use according to the first aspect of the invention.

The pharmaceutical composition of the invention may be used to prevent or treat liver damage. The pharmaceutical composition of the invention can reduce some pathological conditions resulted from liver damage and/or decrease the level of some aminotransferase in serum, and preferably reduce the pathology score as described in the embodiment of the invention or decrease the level of glutamic-pyruvic transaminase or glutamic-oxalacetic transaminase in serum. The pharmaceutical composition of the invention has the ability to induce cytokines such as γ-IFN, IL-4, and IL-10, and antibodies. Thus, preferably the pharmaceutical composition of the invention the invention may be used further to treat and/or prevent Hepatitis C.

A "pharmaceutically acceptable carrier" used herein refers to nontoxic solid, semisolid, or liquid filler, diluent, adjuvant, coating agent or other supplement material for formulation. Depending upon the therapeutic purpose and the route of administration, the pharmaceutical composition may be formulated by well-known techniques in the art as a variety of formulations. Such composition may preferably be presented in unit dosage form, such as tablet, film, ovule, capsule (including sustained-release or delayed-release form), powder, granule, tincture, syrup or emulsion, sterile injectable solution or suspension, aerosol or spray, drop, injection, autotransfusion device or suppository. For example, it may be administered in the form of tablets or capsules. The active medical ingredients as mentioned above may be combined with a kind of nontoxic pharmaceutically acceptable oral inert carrier, such as ethanol, isotonic glucose solution, glycerol, physiological saline, or combinations thereof. The composition may further comprise other supplement materials including, for example, protein protection agents such as human serum albumin, peptide having low molecular weight, amino acid, and metal cation, and adjuvants, such as Freund's complete adjuvant, Freund's incomplete adjuvant, and poly (CpG), etc.

However, it is surprising that the pharmaceutical composition of the invention by itself, without any adjuvants, is capable of preventing or treating liver damage, and/or of preventing or treating Hepatitis C, wherein the said composition comprises a peptide having the sequence of Formula I or a pharmaceutically acceptable salt or ester thereof. In one embodiment, without any adjuvants, the peptide of the invention can significantly increase the amount of interferon secreted from the body. In another embodiment, without any adjuvants, the peptide of the invention can significantly reduce liver damage. These facts suggest, the mechanisms whereby the peptide of the invention prevents or treats liver damage and Hepatitis C are not limited to the inducement of immune response against HCV. The peptide of the invention, when inhibiting virus replication and eliminating virus, might further inhibit excessive immune inflammatory reaction in the body, and thereby achieve the reduction of the damage of liver tissues and cells. Thus, the composition of the second aspect of the invention preferably comprises no adjuvant.

In the peptide having the sequence of Formula I in the pharmaceutical composition of the invention, preferably Xaa1 is Gly, Xaa2 is Thr, Xaa3 is Tyr, and Xaa4 is absent, Ala or Gly, more preferably Xaa4 is absent.

Furthermore, the invention also relates to a use of the pharmaceutical composition of the second aspect of the invention in the manufacture of a medicament for preventing or treating liver damage; the invention also relates to a use of the pharmaceutical composition of the second aspect of the invention in preventing or treating liver damage. Preferably, the use as mentioned above may further include the use for treating and/or preventing Hepatitis C.

The pharmaceutical composition of the invention can be administered by any routes well known to a person skilled in the art, for example, oral, rectal, sublingual, intrapulmonary, transdermal, iontophoretic, vaginal, and intranasal administration. Preferably, the pharmaceutical composition of the invention is administered by parenteral routes, such as subcutaneous, intramuscular or intravenous injection. The dosage to be administered will vary depending upon the formulation, the desired time-course and the subject to be treated, and a physician can readily determine the feasible dosage in the therapy based on the practical situation (e.g., the condition of the patient, body weight and so on). For a general adult, the dosage of the pharmaceutical composition of the invention may be 1 ng-10 g of the peptide having the sequence of Formula I per kg body weight of the adult. For the route of injection, the dosage preferably is 100 ng-10 mg per kg body weight, more preferably 1 μg-1 mg per kg, and most preferably 10 μg-100 μg per kg. For the oral administration, the daily dosage to be administered may be 1 μg-10 g per kg body weight, preferably 10 μg-1 g per kg body weight, and more preferably 100 μg-10 mg.

In the third aspect, the invention provides a peptide having the sequence of Formula I or a pharmaceutically acceptable salt or ester thereof, Xaa1-Gln-Xaa2-Xaa3-Thr-Ser-Gly-Xaa4    (Formula I)

wherein,
Xaa1 is absent, Ala, Gly, Val, Leu or Ile,
Xaa2 is Thr or Ser,
Xaa3 is Tyr, Phe or Trp, and
Xaa4 is absent, Ala, Gly, Val, Leu, Ile or Pro, for the use according to the first aspect of the invention or used in the pharmaceutical composition according to the second aspect of the invention. In the formula, preferably Xaa1 is Gly, Xaa2 is Thr, Xaa3 is Tyr, and Xaa4 is absent, Ala or Gly, more preferably Xaa4 is absent.

The peptide of the invention is a purified peptide with at least 80% pure, preferably at least 90% pure, more preferably at least 95% pure, and particularly with pharmaceutical purity, i.e. at least 98% pure, and pathogen-free and pyrogen-free. Preferably, the peptide of the invention may substantially comprise no other polypeptides or proteins, especially those derived from animals.

Furthermore, in the fourth aspect, the invention provides a polynucleotide encoding the peptide according to the third aspect of the invention. A "polynucleotide" used herein refers to a single stranded or double stranded polymer of deoxyribonucleotides or ribonucleotides, with the sequence reading from 5' end to 3' end, including RNA and DNA. It may be prepared by isolation from the natural source, in vitro synthesis, or recombinant expression.

In the fifth aspect, the invention provides a method of manufacturing a peptide or a pharmaceutically acceptable salt or ester thereof according to the third aspect of the invention, wherein the method comprises the step of chemically synthesizing the said peptide or expressing the said peptide in the fusion form. The method of manufacturing of the invention may further comprise a reaction step for generating the said salt or ester from the said peptide.

It is obvious for a skilled person in the art to chemically synthesize a peptide of known structure. For further details, see the following publications, for example, for the solid phase peptide synthesis, see J. M. Steward and J. D. Young, Solid Phase Peptide Synthesis, the $2^{nd}$ Edition, Pierce Chemical Co., Rockford, Ill. (1984), and J. Meienhofer, Hormonal Proteins and Peptides, Volume 2, Academic Press, New York (1973), etc; and for the liquid phase peptide synthesis, see E. Schroder and K. Lubk, The Peptides, Volume 1, Academic Press, New York (1965), etc. In an embodiment of the invention, the peptides of the invention are synthesized by solid phase synthesis.

It is obvious for a skilled person in the art to express a peptide of known structure in the fusion form and to purify it. (See, for example, Sambrook et al, Molecular Cloning: A Laboratory Manual, the $2^{nd}$ Edition, Cold Spring Harbor Laboratory Press, Cold Spring Harbor, N.Y., 1989; and Ausubel et al, Ed., Current Protocols in Molecular Biology, John Wiley and Sons, Inc. NY, 1987). The said peptide may be prepared by introducing the polynucleotides according to the fifth aspect of the invention into an expression vector and expressing it by a host cell. Suitable vectors include plasmid, cosmid, phage, or virus, and the like; and suitable host cells include bacterium, fungus, and eukaryotic cell.

The publications cited in the application are used to illustrate the invention, the contents of which are incorporated herein by reference, as if they have been written down herein.

For a better understanding of the invention, it will now be described in greater detail by reference to specific Examples. It should be noted that the examples only exemplify the invention, and should not be construed as limiting the scope of the invention. According to the description of the application, various modifications and alterations of the invention are obvious to a skilled person in the art.

EXAMPLES

Example 1

Synthesis of Peptides

Three peptides of the following sequences were synthesized by solid phase peptide synthesis using Model 413A Automatic Peptide Synthesizer (purchased from Perkin Elmer Corporation): GQTYTSG (referred hereinafter to as "Peptide A"), GQTYTSGA (referred hereinafter to as "Peptide B") and GQTYTSGG (referred hereinafter to as "Peptide C"). All of amino acids in the three peptides are L-amino acids. The detailed synthesis was as follows: at first, the reactive groups of the amino acid monomers were protected by protecting groups, i.e., 9-fluorenylmethoxycarbonyl (Fmoc) groups for the α-amino groups of amino acids, teriarybutyl groups for the side chains of Ser and Thr, and trityl (Trt) groups for the side chains of Gln. Then the coupling of the protected amino acids was performed successively with N,N-diisopropylcarbodiimide/1-hydroxylbenzotriazole as coupling agent, for 40 min for each amino acid. In the presence of 15% of dithioglycol/dimethyl thioether/anisole (1:1:1 of volume), the cleavage of the peptides from the resin substrate was performed with trifluoroacetic acid (85%) at room temperature for 120 min, while the protecting groups were removed. Subsequently the resultant peptides were precipitated in anhydrous ether, and then washed several times with anhydrous ether, so as to completely remove mercaptan. After precipitating in water/tertbutyl alcohol (1:1) and then freeze-drying, the raw peptides were made. Within 30 min, the raw peptides were purified by reverse phase HPLC with the gradient of 37-42% acetonitrile/0.9% TFA. After concentrating and then freeze-drying, Peptide A, Peptide B, and Peptide C were made respectively. All of the three peptides were white solids with at least 98% pure.

Example 2

Preparation of a Peptide Conjugate

Peptide A was conjugated to bovine serum albumin (BSA) by glutaraldehyde to generate a conjugate. The detailed conjugation process was as follows: 1 mg of Peptide A synthesized in Example 1 was dissolved into 0.5 ml PBS (pH7.4, 0.02 mol/L); and 4.5 mg of BSA was dissolved into 4.5 ml PBS (pH7.4, 0.02 mol/L). The resultant Peptide A solution was mixed with the BSA solution, and then added gently to 1 ml of 0.1% glutaraldehyde. The conjugation reaction was performed for 12 hours at room temperature in the dark. Then glycine solution (1 mol/L) was added gently to quench the reaction, before dialysis into PBS (pH7.4, 0.02 mol/L) overnight, and then freeze-drying. The resultant Peptide A-BSA conjugate product was referred to as Peptide Conjugate A.

Example 3

Reactivity of the Peptides to Sera of Patients with Hepatitis C 3.1 Sources of Sera Anti-HCV antibody-positive sera: randomly obtained from inpatients infected with HCV in the Liberation Army 302 Hospital from 2000 to 2001.

Control sera: obtained from healthy blood donors, who had normal blood indexes in each assay.

Sera of patients with Hepatitis B (HBV): obtained from inpatients with Hepatitis B in the Liberation Army 302 Hospital, who was positive for the surface antigen of Hepatitis B virus as assayed.

3.2 Method of Determining Reactivity to Sera by Indirect ELISA Assay

The reactivity of the individual peptide of the invention to sera was detected by standard indirect ELISA technology using Model DG3022 Enzyme-Linked Immunoassay Analyzer (purchased from Perkin Elmer Corporation). 10 µg of Peptide A, Peptide B, Peptide C, and Peptide Conjugate A were added respectively into the basic coating buffer (0.1 mol/L NaHCO$_3$, 35 µl; 0.1 mol/L Na$_2$CO$_3$, 15 µl; H$_2$O, 50 µl), and then transferred into the wells of polypropylene/ethylene microtiter plate, and placed at 4° C. overnight. After adding 120 µl of FCS-PBS, each well was blocked at 37° C. for 2 hours. Sera (dilution of 1:100) were then added to the wells, and incubated at 37° C. for 1 hour. Goat anti-human IgGs (dilution of 1:1000) (purchased from Sino-American Biotechnology Company, Beijing) were then added to the wells, and incubated at 37° C. for 1 hour. 50 µl of Solution A and Solution B (purchased from Beijing Kewei Reagent Company) were added to every well, placed in the dark for 5 min, and then the absorbance at 450 nm was measured.

3.3 Results

All of the peptides (Peptide A, Peptide B, Peptide C, and Peptide Conjugate A) are negative for sera of 10 patients with HBV and for sera of 10 heathy donors in ELISA Assay. The results of reactivity of the peptides to anti-HCV antibody-positive sera (of 30 patients) are shown in Table 2. As calculated by $X^2$-test of SATA software, when compared to the reactivity to sera of patients with HBV and heathy donors, Peptide A, Peptide B, Peptide C, and Peptide Conjugate A of the invention can significantly react to sera of patients with HCV, and the conjugate of coupling the peptide to bovine serum albumin results in the increase in the reactivity of the peptide of the invention to sera of patients with HCV.

TABLE 2

Reactivity of the Peptides of the Invention to Sera of Patients with HCV

| Peptide | The Number of Positive Cases | Percentage of Positive Cases (%) |
|---|---|---|
| Peptide A | 13 | 43 |
| Peptide B | 15 | 50 |
| Peptide C | 14 | 47 |
| Peptide Conjugate A | 23 | 77 |

Example 4

Study on In Vivo Immunogenicity of Peptides and Cytokines in Sera in Mice 4.1 Animals BALB/c Mice, all of which are male, 6 week old, and purchased from the Laboratory Animal Center of Academy Of Military Medical Sciences, Beijing, were divided into 4 groups as follows with 5 mice in each group: (1) the control group; (2) the Peptide A group, immunized with Peptide A; (3) the Peptide B group, immunized with Peptide B; and (4) the Peptide C group, immunized with Peptide C.

4.2 Method of Immunization

50 µl of the peptide (100 µg/µl) used in the corresponding group and 50 µl of Freund's complete adjuvant (GIBCOBRL Corp.) were mixed thoroughly with a microstirrer, and the mixture was injected into the claw pad of a mouse, thereby the first immunization was performed for each of the mice. 14 days later, booster immunization was performed in the same manner as the first immunization with 50 µl of the peptide (100 µg/µl) used in the corresponding group and 50 µl of Freund's complete adjuvant (GIBCOBRL Corp.). 14 days later, another booster immunization was performed in the same manner. 14 days later, boost immunization was performed by injecting 100 µg of the peptide dissolved in 200 µl PBS into the mouse intramuscularly. During the process of immunization, only the corresponding adjuvant and PBS were injected for the control group. At the first day after the fourth immunization, mice were sacrificed and sera were collected.

4.3 Determination of Levels of Antibodies in Sera of Mice by ELISA Assay

Figure 1:
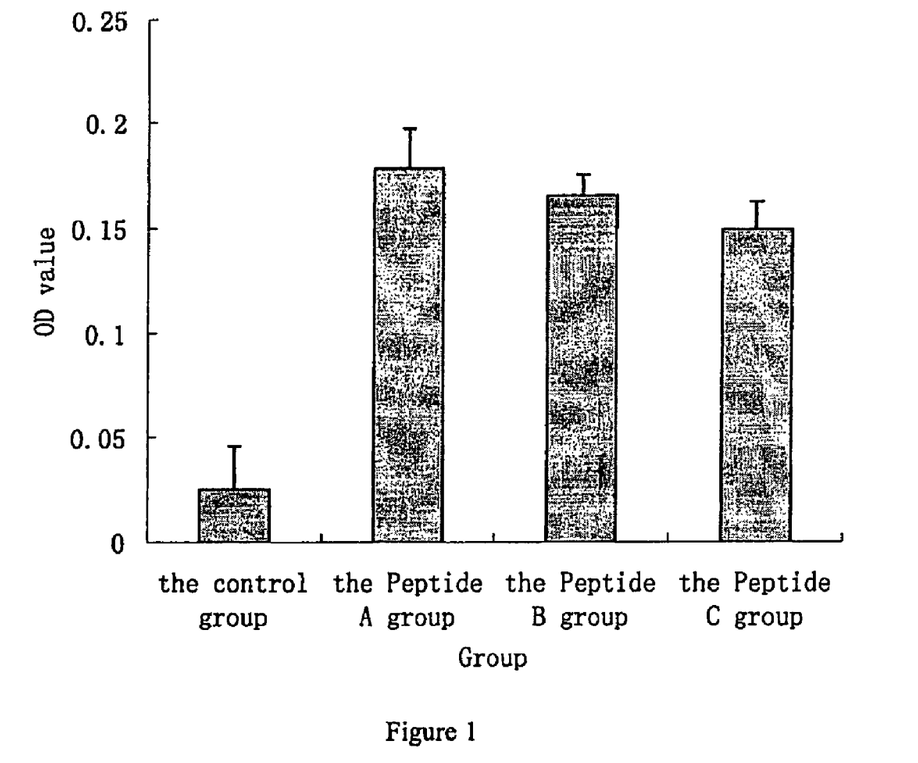
FIG. 1. The levels of various antibodies in sera of the mice immunized with the peptides of the invention.

The antibodies in sera of mice were detected by standard indirect ELISA technology. The wells of polypropylene/ethylene microtiter plate were coated with Peptide A, Peptide B, and Peptide C respectively, namely 10 µg of the above peptides in 100 µl of basic coating buffer coated each well of the plate respectively, and placed at 4° C. overnight. Then the plate was blocked with 120 µl PBS, and incubated at 37° C. for 2 hours. Sera (dilution of 1:100) from the mice of each group were then added to each well, and incubated at 37° C. for 1 hour. 100 µl of Goat anti-mouse IgGs (dilution of 1:1000) (purchased from Sino-American Biotechnology Company, Beijing) were added to each well, and incubated at 37° C. for 1 hour. Then, 50 µl of Solution A and Solution B (purchased from Beijing Kewei Reagent Company) were added, and placed in the dark for 5 min, before measuring the optical density (OD) at 450 nm. The results are shown in FIG. 1.

The above results show that all of the mice immunized with the above peptides can induce considerable humoral immune response in the bodies.

4.4 Determination of Levels of Cytokines in Sera of Mice by ELISA Assay

According to the specification of the manufacturer, the levels of cytokines (i.e., IL-4, IL-10, and γ-IFN) in sera of the above immunized mice were detected respectively by using IL-4 Quantikine ELASA Kit, IL-10 Quantikine ELASA Kit, and γ-IFN Quantikine ELASA Kit (all of which are purchased from R&D, Inc.). The results are shown in Table 3.

TABLE 3 the Levels of Cytokines in Sera of the Immunized Mice

| Group | IL-4 (pg/ml serum) | IL-10 (pg/ml serum) | γ-IFN (pg/ml serum) |
| --- | --- | --- | --- |
| The control group | 2.6 ± 0.1 | 5.86 ± 1.0 | 5.9 ± 0.2 |
| The Peptide A group | 29.64 ± 4.9 | 27.94 ± 6.4 | 23.46 ± 5.9 |
| The Peptide B group | 30.64 ± 4.9 | 27.94 ± 6.4 | 28.46 ± 5.9 |
| The Peptide C group | 31.22 ± 5.0 | 26.926 ± 5.8 | 24.81 ± 5.8 |

The above results show that immunization with the above peptides results in a significant increase in γ-IFN, IL-4, and IL-10 in sera of the mice. γ-IFN, a significant cytokine secreted from Th1, is one of important cytokines against virus infection in immune system of the body, which can activate RNase L by inducement of 2-5 A synthetase to degrade viral RNA, so as to inhibit the synthesis of viral proteins. Therefore, the increased level of γ-IFN suggests that the above peptides can be used to eliminate HCV.

Example 5

Effects of the Peptide on γ-IFN of Rats In Vivo 5.1 Animals

SD Rats (body weight of each was 180 g~220 g; half of them were male and the others were female; and they were purchased from the Animal Institute of Academy Of Military Medical Sciences) were divided randomly into 5 groups as follows with 10 rats in each group: (1) the blank control group; (2) the adjuvant control group; (3) the high dose group, immunized with Peptide A and adjuvant; (4) the low dose group, immunized with Peptide A and adjuvant; and (5) the peptide group, immunized with Peptide A only.

5.2 Methods

Rats in the high dose group and the low dose group were immunized as follows: At Day 0, the first immunization was performed by the following process: Peptide A dissolved in physiological saline was mixed thoroughly with the equivalent volume of Freund's complete adjuvant, and then 0.1 ml of the resultant water-in-oil emulsion was administered via subcutaneous injection to each rat, wherein the dosage of Peptide A contained in the emulsion was 50 μg/kg rat body weight for the high dose group and 25 μg/kg rat body weight for the low dose group respectively. 4 days later, the second immunization was performed in the same dosage and manner as the first immunization except that, Freund's complete adjuvant was replaced by Freund's incomplete adjuvant. 4 days later, the third immunization was performed in the same dosage and manner as the first immunization except that, Freund's complete adjuvant was replaced by Freund's incomplete adjuvant. 4 days later, the fourth immunization was performed by the following process: 0.1 ml of Peptide A dissolved in physiological saline was administered without any adjuvants via intraperitoneal injection to each rat, wherein the dosage of Peptide A was 50 μg/kg rat body weight for the high dose group and 25 μg/kg rat body weight for the low dose group respectively. During the process of immunization, starting at Day 0, only the corresponding adjuvant and physiological saline without Peptide A were injected into each rat of the adjuvant control group at the days of immunization; and only physiological saline was injected into each rat of the blank control group at the days of immunization.

At the days of immunization for the high dose group and the low dose group, starting at Day 0, 0.1 ml of Peptide A dissolved in physiological saline without any adjuvants was administered via subcutaneous injection to each rat of the peptide group, for immunization up to four times, wherein the dosage of Peptide A was 50 μg/kg rat body weight for every immunization.

At the first day after the fourth immunization, rats from every group were sacrificed and splenocytes were collected. The splenocytes were then added into the culture plate at $1 \times 10^6$ cells/well, incubated at 37° C. for 3 days, and then the supernatant of the culture was collected. According to the specification of the manufacturer, the level of γ-IFN in sera of the above immunized rats was detected by using γ-IFN ELASA Quantikine ELASA Kit (purchased from R&D, Inc.).

5.3 Results

Figure 2:
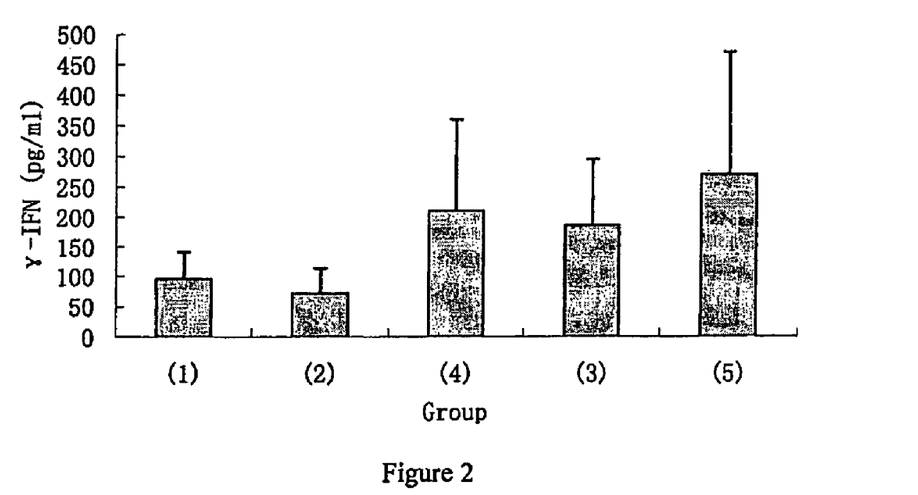
FIG. 2. The amount of γ-IFN secreted from splenocytes of the rats inoculated with the peptides of the invention with or without adjuvants.

The results for the level of γ-IFN in sera of rats are shown in FIG. 2. The results show that when compared to both of the control groups, there is a significant increase in γ-IFN in sera of the immunized rats. It is surprising that the level of γ-IFN in sera of the rats immunized only with Peptide A and with no adjuvant is even higher than that with the same dosage of Peptide A and adjuvant.

Example 6

Protective Effects of the Peptide on BCG Vaccine and Lipopolysaccharide-Induced Immunological Liver Damage of Rats 6.1 Animals Wistar Rats (body weight of each was 180 g~220 g; half of them were male and the others were female; and they were purchased from Shanghai Slac Laboratory Animal, Inc.) were divided randomly into 8 groups as follows with 10 rats in each group: (1) the diammonium glycyrrhizinate injection group, injected with diammonium glycyrrhizinate purchased from Jiangsu Chia-tai Tianqing Pharmaceutical Co. Ltd.; (2) the interferon group, injected with recombinant human interferon-α2a purchased from Shenyang Sunshine Pharmaceutical Co., Ltd.; (3) the high dose group, immunized with Peptide A; (4) the medium dose group, immunized with Peptide A; (5) the low dose group, immunized with Peptide A; (6) the low dose & adjuvant group, immunized with Peptide A and adjuvant; (7) the blank control group; and (8) the model group.

6.2 Methods

Rats in the low dose & adjuvant group were immunized as follows: At Day 0, the first immunization was performed by the following process: 50 μl of Peptide A dissolved in physiological saline was mixed thoroughly with the equivalent volume of Freund's complete adjuvant, and then 0.1 ml of the resultant water-in-oil emulsion was administered via subcutaneous injection to each rat, wherein the dosage of Peptide A contained in the emulsion was 43.5 μg/kg rat body weight. 4 days later, the second immunization was performed in the same dosage and manner as the first immunization except that, Freund's complete adjuvant was replaced by Freund's incomplete adjuvant. 4 days later, the third immunization was performed in the same dosage and manner as the first immunization except that, Freund's complete adjuvant was replaced by Freund's incomplete adjuvant. 4 days later, the fourth immunization was performed by the following process: 0.1 ml of Peptide A dissolved in physiological saline was administered without any adjuvants via intraperitoneal injection to each rat, wherein the dosage of Peptide A was 43.5 μg/kg rat body weight.

At the days of immunization for the low dose & adjuvant group, starting at Day 0, 0.1 ml of Peptide A dissolved in physiological saline was administered without any adjuvants via subcutaneous injection to each rat of the high dose group, the medium dose group, and the low dose group, for immunization up to four times, wherein for every immunization, the dosage of Peptide A was 174, 87, and 43.5 μg/kg rat body weight respectively for the high dose group, the medium dose group, and the low dose group.

At the days of immunization for the low dose & adjuvant group, starting at Day 0, 0.1 ml of physiological saline was injected into each rat of the model group and the blank control group.

And at the $9^{th}$ day before the fourth immunization, after Polysaccharide and Nucleic Acid fraction of Bacillus Calmette Guerin for Injection, which was produced by Hunan Jiuzhitang Siqi Biopharmaceutical Co., Ltd. and comprised 0.35 mg polysaccharide of Bacillus Calmette Guerin per milliliter, was diluted with physiological saline, 0.2 ml of the diluted product was intravenously injected into the tail of each rat of the 7 groups other than the blank control group, at the dosage 126 μg polysaccharide of Bacillus Calmette Guerin/kg rat body weight; meanwhile, the equivalent volume of physiological saline was injected for the blank control group. At the third day after the fourth immunization, 10 μg of lipopolysaccharide (LPS, available from SIGMA, Inc.) was administered via intravenous injection to each rat of the 7 groups other than the blank control group; meanwhile, the equivalent volume of physiological saline was injected for the blank control group.

In addition, from the $7^{th}$ day before injecting LPS on, diammonium glycyrrhizinate was administered via intraperitoneal injection to each rat of the diammonium glycyrrhizinate injection group every day, at the dosage of 13.5 mg diammonium glycyrrhizinate/kg rat body weight, lasting for 7 days; and from the $7^{th}$ day before injecting LPS on, interferon was administered via intraperitoneal injection to each rat of the interferon group every day, at the dosage of 540 thousand units/kg rat body weight, lasting for 7 days.

At the $12^{th}$ hour after injecting lipopolysaccharide, each rat was weighed and then sacrificed by cervical dislocation, before blood was collected. After sera were isolated, according to the specification of the manufacturer, the activities of glutamic-pyruvic transaminase (SGPT) and glutamic-oxalacetic transaminase (SGOT) in sera were detected respectively by using Glutamic-pyruvic Transaminase Detection Kit (purchased from Nanjing Jiancheng Bioengineering Institute) and Glutamic-oxalacetic Transaminase Detection Kit (purchased from Nanjing Jiancheng Bioengineering Institute). At the same time, after the livers obtained from the rats were fixed in 10% formalin, and then dehydrated, coated with paraffin, sliced (4 μm thick), and HE stained, the professional pathologist examined them under the optical microscope for the following pathological conditions and scored: (1) degeneration of live cells, including steatosis, liver edema, acidophilic degeneration and the like; (2) necrosis of liver cells, including spotty necrosis, focal necrosis and the like; (3) dilatation and congestion of central vein and hepatic sinus, and perivasculitis of liver; (4) connective tissue proliferation or inflammatory cell infiltration in liver and portal area. According to the severity of each pathological condition, the criteria of pathological condition score are defined as 0 for normal, 0.5 for extremely minor, 1 for minor, 2 for medium, 3 for severe, and 4 for extremely severe, and double scored in the presence of focal necrosis. Then the average score was calculated for each group of animals, and the more average score represents the worse pathological conditions.

6.3 Results

Figure 3:
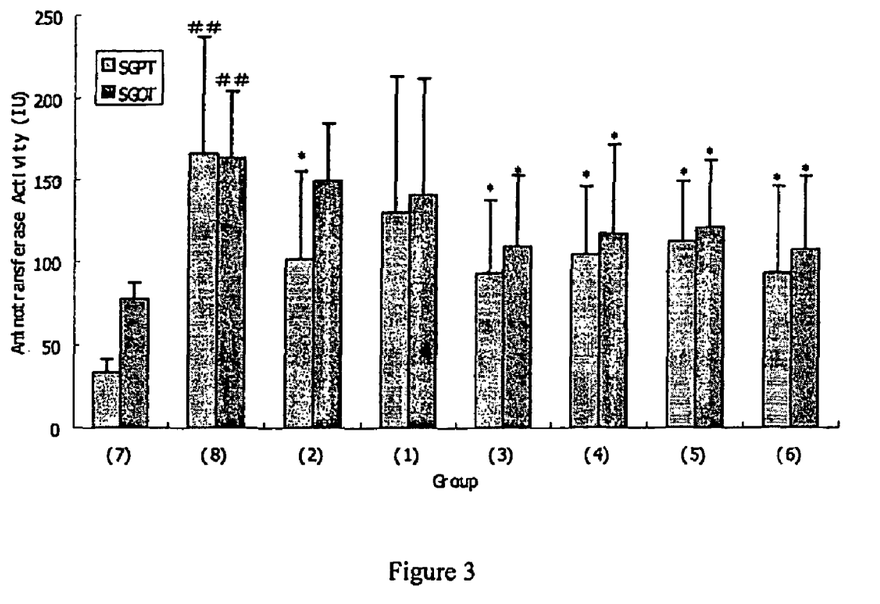
FIG. 3. The effects on biochemical criteria of sera in the model of BCG vaccine and lipopolysaccharide-induced immunological liver damage of rat after immunization with the peptides of the invention, in which * indicates that the corresponding group can significantly decrease the level of aminotransferase relative to the model group.
Figure 4:
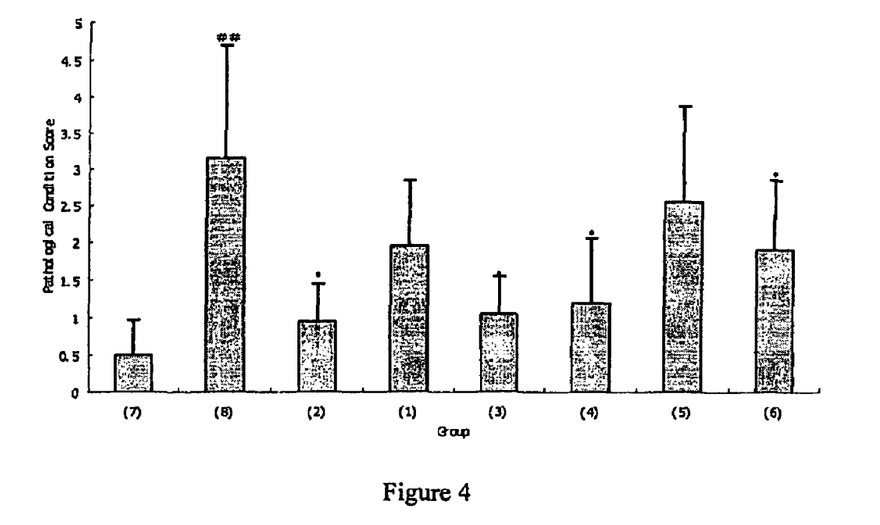
FIG. 4. The scores of pathological conditions of liver in the model of BCG vaccine and lipopolysaccharide-induced immunological liver damage of rat after immunization with the peptides of the invention, in which * indicates that the corresponding group can significantly alleviate the pathological conditions of liver relative to the model group.

The results of activities of glutamic-pyruvic transaminase (SGPT) and glutamic-oxalacetic transaminase (SGOT) are shown in FIG. 3, and the results of the pathological condition scores are shown in FIG. 4.

There is a significant increase in glutamic-pyruvic transaminase and glutamic-oxalacetic transaminase in sera of rats in the model group, indicating that BCG vaccine and lipopolysaccharide can cause immunological liver damage of rats. Peptide A at high, medium, and low dosage can result in a significant decrease in the levels of glutamic-pyruvic transaminase and glutamic-oxalacetic transaminase of rats with liver damage, and the protective effect on acute immunological liver damage is also shown in the low dose & adjuvant group. Namely, in the model of BCG vaccine and lipopolysaccharide-induced immunological liver damage of rat, Peptide A can result in a significant decrease in the levels of glutamic-pyruvic transaminase and glutamic-oxalacetic transaminase of the rat with immunological liver damage, however, diammonium glycyrrhizinate injection has no significant protective effect on liver damage of rats.

The study on pathological histology indicates that the experiment has successfully reproduced the model of immunological liver damage. The pathological conditions of liver tissues obtained from the model group have been shown to include spotty necrosis of liver cells and some focal necrosis; the increased amount of neutrophilic granulocytes in liver, particularly around central vein; and minor inflammatory cell infiltration in portal area. The results of pathological condition score show that when compared to the model group, the pathological conditions of the animals in the high dose group, the medium dose group, the low dose & adjuvant group and the interferon group have been alleviated significantly ($P<0.05$). Namely, Peptide A at high and medium dosage without any adjuvants and Peptide A at low dosage with adjuvant, can result in a significant alleviation in pathological condition of liver, however, diammonium glycyrrhizinate injection has no significant protective effect on liver damage of rats.

Example 7

Protective Effects of the Peptide on D-Aminogalactose-Induced Acute Liver Damage of Rats 7.1 Animals Wistar Rats (body weight of each was 180 g~220 g; half of them were male and the others were female; and they were purchased from Shanghai Slac Laboratory Animal, Inc.) were divided randomly into 6 groups as follows with 10 rats in each group: (1) the diammonium glycyrrhizinate injection group, injected with diammonium glycyrrhizinate; (2) the high dose group, immunized with Peptide A and adjuvant; (3) the medium dose group, immunized with Peptide A and adjuvant; (4) the low dose group, immunized with Peptide A and adjuvant; (5) the blank control group; and (6) the model group.

7.2 Methods

Rats in the high dose group, the medium dose group and the low dose group were immunized as follows: At Day 0, the first immunization was performed by the following process: 100 µl of Peptide A dissolved in physiological saline was mixed thoroughly with the equivalent volume of Freund's complete adjuvant, and then 0.2 ml of the resultant water-in-oil emulsion was administered via subcutaneous injection to each rat, wherein the dosage of Peptide A contained in the emulsion was 174 µg/kg rat body weight for the high dose group, 87 µg/kg rat body weight for the medium dose group, and 43.5 µg/kg rat body weight for the low dose group respectively. 14 days later, the second immunization was performed in the same dosage and manner as the first immunization except that, Freund's complete adjuvant was replaced by Freund's incomplete adjuvant. 14 days later, the third immunization was performed in the same dosage and manner as the first immunization except that, Freund's complete adjuvant was replaced by Freund's incomplete adjuvant. 14 days later, the fourth immunization was performed by the following process: 0.1 ml of Peptide A dissolved in physiological saline was administered without any adjuvants via intraperitoneal injection to each rat, wherein the dosage of Peptide A was 174 µg/kg rat body weight for the high dose group, 87 µg/kg rat body weight for the medium dose group, and 43.5 µg/kg rat body weight for the low dose group respectively.

At the days of immunization for the high dose group, the medium dose group and the low dose group, starting at Day 0, the corresponding physiological saline was injected into each rat of the model group and the blank control group, for up to four times.

At the $24^{th}$ hour after the fourth immunization, 0.2 ml of D-aminogalactose (available from SIGMA, Inc.) was administered via intraperitoneal injection to each rat of the 5 groups other than the blank control group, at the dosage of 600 mg/kg rat body weight; meanwhile, the equivalent volume of physiological saline was injected for the blank control group. At the $48^{th}$ hour after intraperitoneally injecting D-aminogalactose, each rat was sacrificed.

In addition, from the $7^{th}$ day before sacrificing each rat on, diammonium glycyrrhizinate was administered via intraperitoneal injection to each rat of the diammonium glycyrrhizinate injection group every day, at the dosage of 13.5 mg diammonium glycyrrhizinate/kg rat body weight, lasting for 7 days.

At the $48^{th}$ hour after intraperitoneally injecting D-aminogalactose, each rat was sacrificed by cervical dislocation, and blood was collected. After sera were isolated, according to the specification of the manufacturer, the activities of glutamic-pyruvic transaminase (SGPT) and glutamic-oxalacetic transaminase (SGOT) in sera were detected respectively by using Glutamic-pyruvic Transaminase Detection Kit (purchased from Nanjing Jiancheng Bioengineering Institute) and Glutamic-oxalacetic Transaminase Detection Kit (purchased from Nanjing Jiancheng Bioengineering Institute).

7.3 Results

Figure 5:
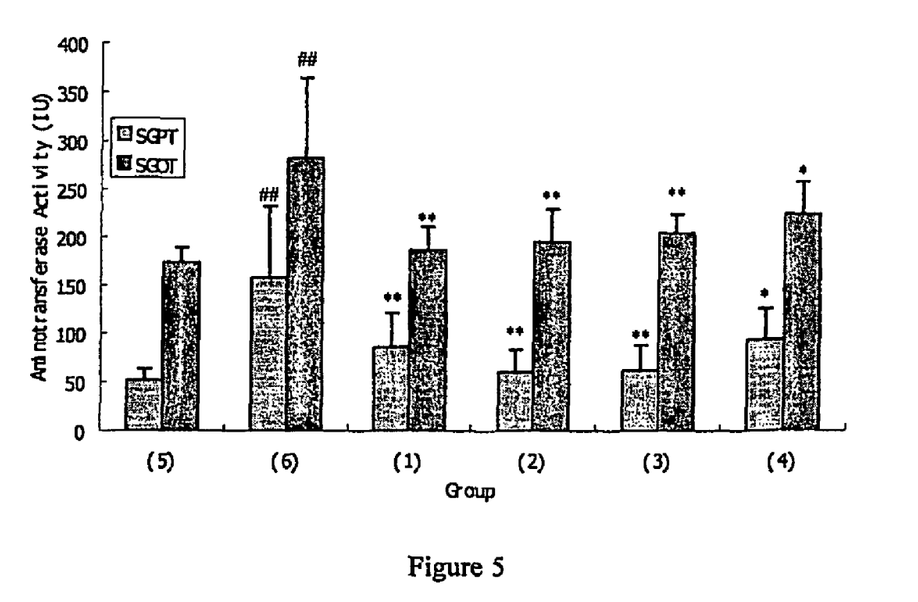
FIG. 5. The effects on biochemical criteria of sera in the model of D-aminogalactose-induced acute liver damage of rat after immunization with the peptides of the invention, in which * indicates that the corresponding group can significantly decrease the level of aminotransferase relative to the model group.

The results are shown in FIG. 5. There is a significant increase in the levels of glutamic-pyruvic transaminase and glutamic-oxalacetic transaminase in sera of rats in the D-aminogalactose model group, indicating that D-aminogalactose can cause acute liver damage of rats. Peptide A at high, medium, and low dosage can result in a significant decrease in the levels of glutamic-pyruvic transaminase and glutamic-oxalacetic transaminase of rats with acute liver damage in the experiment, and the diammonium glycyrrhizinate injection is also shown to have the significant protective effect on acute liver damage of rats.

Example 8

Protective Effects of the Peptide on Tetrachloromethane-Induced Liver Damage of Mice 8.1 Animals BALB/c mice, each of which is 18 g~22 g weight, and purchased from Shanghai Slac Laboratory Animal, Inc., were divided randomly into 8 groups as follows with 10 rats in each group: (1) the diammonium glycyrrhizinate injection group, injected with diammonium glycyrrhizinate; (2) the interferon group, injected with recombinant human interferon-α2a); (3) the high dose group, immunized with Peptide A and adjuvant; (4) the medium dose group, immunized with Peptide A and adjuvant; (5) the low dose group, immunized with Peptide A and adjuvant; (6) the adjuvant control group, immunized with adjuvant only; (7) the blank control group; and (8) the model group.

8.2 Methods

At the first before the first immunization, 0.05 ml $CCl_4$ (available from Shanghai Linfen Chemical Reagent Co., Ltd.) was administered via subcutaneous injection to each mouse of all groups other than the blank control group; and the equivalent volume of physiological saline was injected for the blank control group.

Mice in the high dose group, the medium dose group and the low dose group were immunized as follows: the first immunization was performed by the following process: 100 µl of Peptide A dissolved in physiological saline was mixed thoroughly with the equivalent volume of Freund's complete adjuvant, and then 0.2 ml of the resultant water-in-oil emulsion was administered via subcutaneous injection to each mouse, wherein the dosage of Peptide A contained in the emulsion was 250 µg/kg mouse body weight for the high dose group, 125 µg/kg mouse body weight for the medium dose group, and 62.5 µg/kg mouse body weight for the low dose group respectively. 14 days later, the second immunization was performed in the same dosage and manner as the first immunization except that, Freund's complete adjuvant was replaced by Freund's incomplete adjuvant. 14 days later, the third immunization was performed in the same dosage and manner as the first immunization except that, Freund's complete adjuvant was replaced by Freund's incomplete adjuvant. 14 days later, the fourth immunization was performed by the following process: 0.1 ml of Peptide A dissolved in physiological saline was administered without any adjuvants via intraperitoneal injection to each rat, wherein the dosage of Peptide A was 250 µg/kg mouse body weight for the high dose group, 125 µg/kg mouse body weight for the medium dose group, and 62.5 µg/kg mouse body weight for the low dose group respectively.

At the days of immunization for the high dose group, the medium dose group and the low dose group, starting at Day 0, the corresponding physiological saline was injected into each rat of the model group and the blank control group, for up to four times; meanwhile, the corresponding adjuvant and physiological saline were injected for the adjuvant control group, for up to four times.

At the first day before the fourth immunization, 0.05 ml $CCl_4$ was administered via subcutaneous injection to each mouse of all groups other than the blank control group; and the equivalent volume of physiological saline was injected for the blank control group. At the second day after the fourth immunization, all of mice were sacrificed.

In addition, from the 7$^{th}$ day before sacrificing each mouse on, diammonium glycyrrhizinate was administered via intraperitoneal injection to each mouse of the diammonium glycyrrhizinate injection group every day, at the dosage of 19.5 mg diammonium glycyrrhizinate/kg mouse body weight, lasting for 7 days; and from the 7$^{th}$ day before sacrificing each mouse on, interferon was administered via intraperitoneal injection to each mouse of the interferon group every day, at the dosage of 750 thousand units/kg mouse body weight, lasting for 7 days.

Just before sacrificing all mice, each rat was weighed, and then sacrificed by cervical dislocation. Then Blood was collected, before sera were isolated. According to the specification of the manufacturer, the activities of glutamic-pyruvic transaminase (SGPT) and glutamic-oxalacetic transaminase (SGOT) were detected respectively by using Glutamic-pyruvic Transaminase Detection Kit (purchased from Nanjing Jiancheng Bioengineering Institute) and Glutamic-oxalacetic Transaminase Detection Kit (purchased from Nanjing Jiancheng Bioengineering Institute). At the same time, after the livers obtained from the mice were fixed in 10% formalin, and then dehydrated, coated with paraffin, sliced (4 μm thick), and HE stained, the professional pathologist examined them under the optical microscope for the pathological conditions and scored in the same manner as Example 6.

8.3 Results

Figure 6:
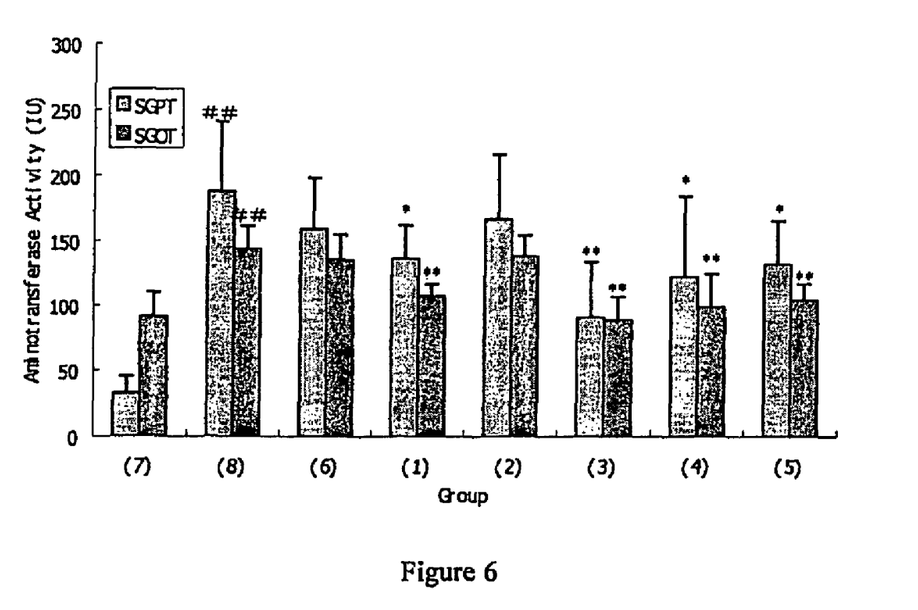
FIG. 6. The effects on biochemical criteria of sera in the model of tetrachloromethane-induced liver damage of mouse after immunization with the peptides of the invention, in which * indicates that the corresponding group can significantly decrease the level of aminotransferase relative to the model group.
Figure 7:
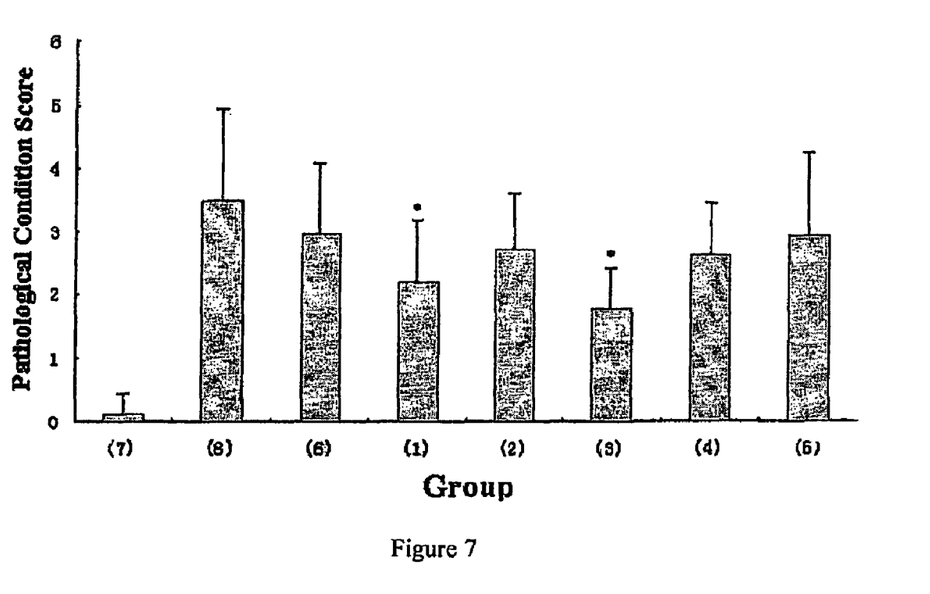
FIG. 7. The scores of pathological conditions of liver in the model of tetrachloromethane-induced liver damage of mouse after immunization with the peptides of the invention, in which * indicates that the corresponding group can significantly alleviate the pathological conditions of liver relative to the model group.

The results of activities of glutamic-pyruvic transaminase (SGPT) and glutamic-oxalacetic transaminase (SGOT) are shown in FIG. 6, and the results of the pathological condition scores are shown in FIG. 7.

There is a significant increase in the levels of glutamic-pyruvic transaminase and glutamic-oxalacetic transaminase in sera of mice in the model group, indicating that tetrachloromethane can cause acute liver damage of mice in the experiment. And Peptide A at high, medium, and low dosage can result in a significant decrease in the levels of glutamic-pyruvic transaminase and glutamic-oxalacetic transaminase of mice with acute liver damage in the experiment. However, interferon and adjuvant have no significant activities to decreasing the level of aminotransferase.

The study on pathological histology indicates that tetrachloromethane can effectively cause acute liver damage. The pathological conditions of liver tissues obtained from the model group have been shown to include spotty necrosis of liver cells or focal necrosis; vasculitis presented in liver; and minor inflammatory cell infiltration and fibroblast proliferation found in portal area. The results of pathological condition score show that when compared to the model group, the pathological conditions of the liver tissues obtained from the high dose group have been alleviated significantly.

In addition, the hepatomegaly of mouse liver is more visible in the mouse of the model group than in that of both control groups. The administration of Peptide A at the dosage of 250 μg/kg mouse body weight can result in a significant reduction in such tetrachloromethane-induced hepatomegaly of mice. However, interferon has no significant activity to reduce tetrachloromethane-induced hepatomegaly of mice.

What is claimed is:

1. A method of treating hepatotoxic chemical substance-induced liver damage, comprising:
 administering to a patient in need thereof, an amount of a peptide having the sequence of Formula I or a pharmaceutically acceptable salt or ester thereof, effective for treating hepatotoxic chemical substance-induced liver damage, Xaa1-Gln-Xaa2-Xaa3-Thr-Ser-Gly-Xaa4 (Formula I)

wherein,
 Xaa1 is absent, Ala, Gly, Val, Leu or Ile,
 Xaa2 is Thr or Ser,
 Xaa3 is Tyr, Phe or Trp, and
 Xaa4 is absent, Ala, Gly, Val, Leu, Ile or Pro, and
 wherein the hepatotoxic chemical substance is $CCl_4$.

2. The method according to claim 1, wherein in the said sequence, Xaa1 is Gly, Xaa2 is Thr, Xaa3 is Tyr, and Xaa4 is absent, Ala or Gly.

3. The method according to claim 2, wherein Xaa4 is absent.

4. A method of treating hepatotoxic chemical substance-induced liver damage, comprising: administering to a patient in need thereof a pharmaceutical composition that contains an amount of a peptide having the sequence of Formula I or a pharmaceutically acceptable salt or ester thereof, effective for treating hepatotoxic chemical substance-induced live damage in the patient, Xaa1-Gln-Xaa2-Xaa3-Thr-Ser-Gly-Xaa4 (Formula I)

wherein,
 Xaa1 is absent, Ala, Gly, Val, Leu or Ile,
 Xaa2 is Thr or Ser,
 Xaa3 is Tyr, Phe or Trp, and
 Xaa4 is absent, Ala, Gly, Val, Leu, Ile or Pro, and
 wherein the hepatotoxic chemical substance is $CCl_4$.

* * * * *

```
                        SEQUENCE LISTING

<160> NUMBER OF SEQ ID NOS: 4

<210> SEQ ID NO 1
<211> LENGTH: 8
<212> TYPE: PRT
<213> ORGANISM: Artificial
<220> FEATURE:
<223> OTHER INFORMATION: Formula I
<220> FEATURE:
<221> NAME/KEY: VARIANT
<222> LOCATION: (1)..(1)
<223> OTHER INFORMATION: Xaa can be absent, Ala, Gly, Val, Leu or Ile
<220> FEATURE:
<221> NAME/KEY: VARIANT
<222> LOCATION: (3)..(3)
<223> OTHER INFORMATION: Xaa can be Thr or Ser
<220> FEATURE:
<221> NAME/KEY: VARIANT
<222> LOCATION: (4)..(4)
<223> OTHER INFORMATION: Xaa can be Tyr, Phe or Trp
<220> FEATURE:
<221> NAME/KEY: VARIANT
<222> LOCATION: (8)..(8)
<223> OTHER INFORMATION: Xaa can be absent, Ala, Gly, Val, Leu, Ile or
      Pro

<400> SEQUENCE: 1

Xaa Gln Xaa Xaa Thr Ser Gly Xaa
1               5

<210> SEQ ID NO 2
<211> LENGTH: 7
<212> TYPE: PRT
<213> ORGANISM: Artificial
<220> FEATURE:
<223> OTHER INFORMATION: Peptide A
```

```
<400> SEQUENCE: 2

Gly Gln Thr Tyr Thr Ser Gly
1               5

<210> SEQ ID NO 3
<211> LENGTH: 8
<212> TYPE: PRT
<213> ORGANISM: Artificial
<220> FEATURE:
<223> OTHER INFORMATION: Peptide B

<400> SEQUENCE: 3

Gly Gln Thr Tyr Thr Ser Gly Ala
1               5

<210> SEQ ID NO 4
<211> LENGTH: 8
<212> TYPE: PRT
<213> ORGANISM: Artificial
<220> FEATURE:
<223> OTHER INFORMATION: Peptide C

<400> SEQUENCE: 4

Gly Gln Thr Tyr Thr Ser Gly Gly
1               5
```